United States Patent
Fabricant

(10) Patent No.: US 8,048,896 B2
(45) Date of Patent: *Nov. 1, 2011

(54) METHODS FOR INHIBITING AND BREAKING AGE COMPLEX FORMATION

(75) Inventor: Jill D. Fabricant, Dana Point, CA (US)

(73) Assignee: Cell Viable Corporation, Corona del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/952,024

(22) Filed: Dec. 6, 2007

(65) Prior Publication Data

US 2008/0076804 A1    Mar. 27, 2008

Related U.S. Application Data

(63) Continuation-in-part of application No. 11/537,967, filed on Oct. 2, 2006.

(60) Provisional application No. 60/894,527, filed on Mar. 13, 2007, provisional application No. 60/868,870, filed on Dec. 6, 2006, provisional application No. 60/724,138, filed on Oct. 5, 2005.

(51) Int. Cl.
  *A61K 31/44* (2006.01)
  *A61K 31/17* (2006.01)
  *A61K 31/18* (2006.01)
  *A61K 31/155* (2006.01)

(52) U.S. Cl. ......... 514/332; 514/596; 514/601; 514/632
(58) Field of Classification Search .................. 514/332, 514/596, 601, 632
  See application file for complete search history.

(56) References Cited

U.S. PATENT DOCUMENTS

| | | | |
|---|---|---|---|
| 4,496,556 A | | 1/1985 | Orentreich |
| 5,334,617 A | * | 8/1994 | Ulrich et al. .................. 514/562 |
| 5,985,587 A | * | 11/1999 | Niman et al. ................. 435/7.23 |
| 6,337,350 B1 | * | 1/2002 | Rahbar et al. ................. 514/596 |
| 6,410,598 B1 | * | 6/2002 | Vitek et al. .................... 514/632 |
| 2004/0137068 A1 | * | 7/2004 | Bhushan ....................... 424/486 |

OTHER PUBLICATIONS

Miyata et al., Mechanism of Inhibitory Effect of OPB-9195 [(±)-2-Isopropylidenehydranzono-4-oxo-thiazolidin-5-ylacetanilide] on Advanced Glycation End Products and Advanced Lipoxidation End Product Formation, Journal of American Society of Nephrology, vol. 11, No. 9, pp. 1719-1725 (2000) in view of Bhushan (US 2004/0137068 A1).*

* cited by examiner

*Primary Examiner* — Kevin E Weddington
(74) *Attorney, Agent, or Firm* — Hedman & Costigan, P.C.; James V. Costigan

(57) ABSTRACT

Various methods of administering medication(s) that inhibit the nonenzymatic formation of glycation and dehydration condensation complexes known as advanced glycation endproducts (AGEs) or modulate the advanced glycation endproduct receptor (RAGE) are provided.

4 Claims, 4 Drawing Sheets

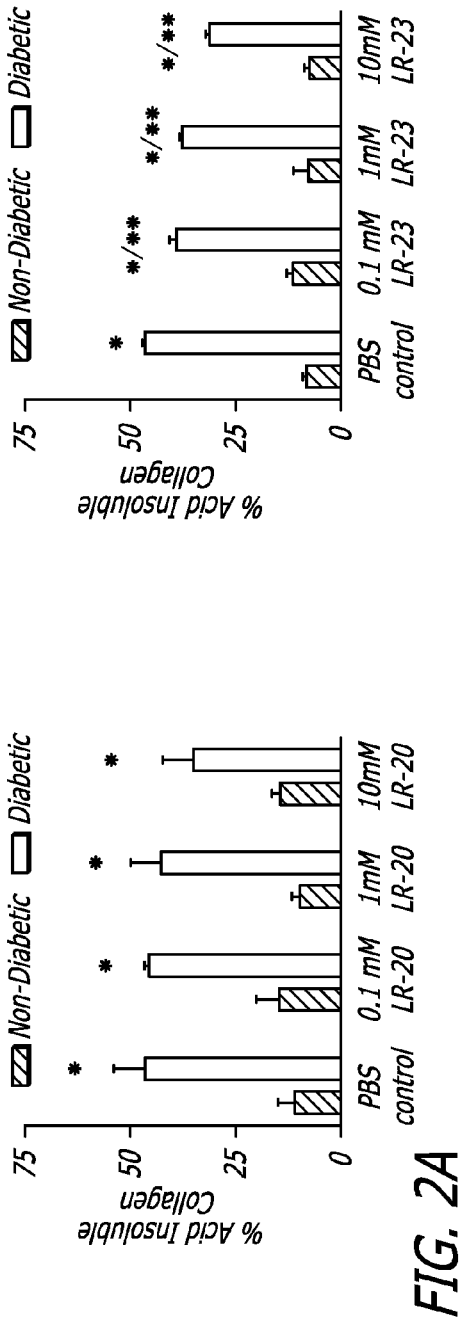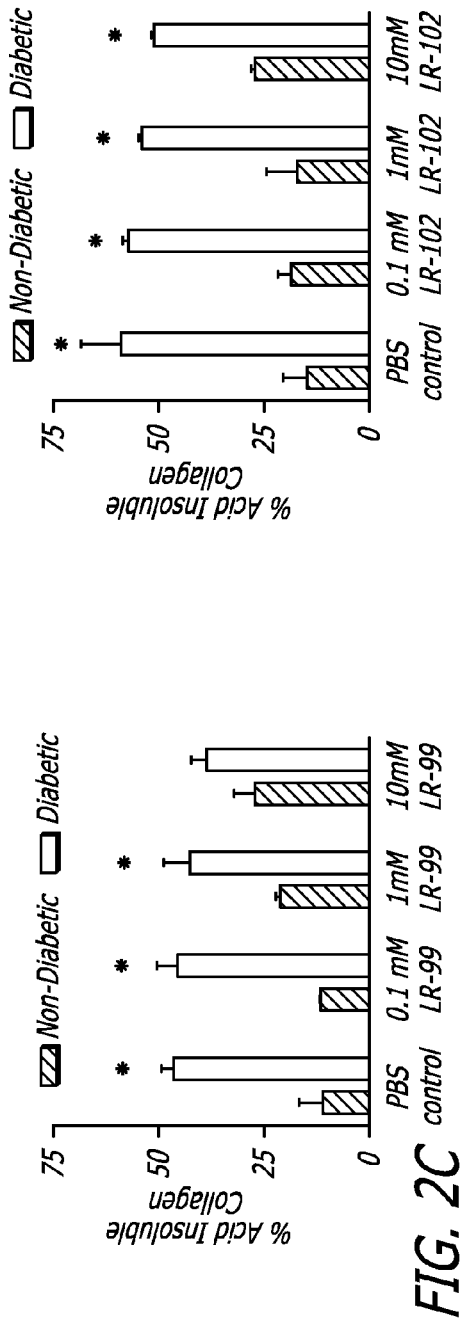

METHODS FOR INHIBITING AND BREAKING AGE COMPLEX FORMATION

CROSS REFERENCE TO RELATED APPLICATIONS

The present application claims the benefit under 35 U.S.C. §119(e) of U.S. Provisional Patent Application Nos. 60/868,870 filed Dec. 6, 2006 and 60/894,527 filed Mar. 13, 2007 and is a continuation-in-part of U.S. patent application Ser. No. 11/537,967 filed Oct. 2, 2006 which in turn claims the benefit under 35 U.S.C. §119(e) to U.S. Provisional Patent Application No. 60/724,138, filed Oct. 5, 2005. The contents of all these applications are incorporated by reference herein in their entirety.

FIELD OF THE INVENTION

The present invention relates to methods of administering medication(s) that inhibit and break the nonenzymatic formation of glycation and dehydration condensation complexes known as advanced glycation end-products (AGE). The present invention also relates to medication releasing formulation comprising at least one medication(s) that inhibits the nonenzymatic formation of glycation and dehydration condensation complexes or causes the breakage of such complexes.

BACKGROUND OF THE INVENTION

An elevated concentration of reducing sugars (i.e., glucose) in the blood and in the intracellular environment of an animal, namely a human, typically results in the nonenzymatic formation of glycation and dehydration condensation complexes known as advanced glycation end-products (AGE). These AGE complex products form on free amino groups, on proteins, on lipids and on DNA (Bucala and Cerami, Adv Pharmacol 23:1-34, 1992; Bucala et al., Proc Natl Acad Sci 90:6434-6438, 1993; Bucala et al., Proc Natl. Acad Sci 81:105-109, 1984). This phenomenon is called "browning" or a "Maillard" reaction and was discovered early in this century by the food industry (Maillard, Ann Chim 5:258-317, 1916). The significance of a similar process in biology became evident only after the discovery of the glycosylated hemoglobins and their increased presence in diabetic patients (Rahbar, Clin Chim Acta 20:381-5, 1968; Rahbar et al., Biochem Biophys Res Commun 36:838-43, 1969). A diabetic patient's AGE level increases markedly as a result of sustained high blood sugar levels and often leads to tissue damage through a variety of mechanisms including alteration of tissue protein structure and function, stimulation of cellular responses through AGE specific receptors and/or the generation of reactive oxygen species (ROS) (for a recent review see Boel et al., J Diabetes Complications 9:104-29, 1995). These AGE have been shown to cause complications in patients suffering from various pathological conditions, including, but not limited to, diabetes mellitus, rheumatoid arthritis, Alzheimer's Disease, uremia and in atherosclerosis in persons undergoing hemodialysis.

Advanced glycation end-products bind to cell surface receptors on a variety of cells including, but not limited to, endothelial cells of the microvasculature, monocytes and macrophages, smooth muscle cells, mesengial cells and neurons through a specific receptor for AGEs, termed RAGE. RAGE is a member of the immunoglobulin super family of cell surface molecules. Increased levels of RAGE are expressed in a number of tissues including, but not limited to, aging tissues, diabetic tissues, the vasculature and the kidney. Activation of RAGE has been implicated in a variety of conditions including, but not limited to, acute and chronic inflammation, in certain complications of diabetes, nephropathy, atherosclerosis and retinopathy, Alzheimer's disease, erectile dysfunction and in tumor invasion and metastases.

The complications associated with each of these aforementioned pathological conditions places a significant burden on afflicted patients. Moreover, these complications have detrimental effects on society in general. As one example, the global prevalence of diabetes mellitus afflicts millions of individuals resulting in significant increases of morbidity and mortality rates. These increased morbidity and mortality rates, together with the great financial burden of treating diabetic complications, are major incentives to search for and develop medications having the potential of preventing or treating complications of the disease.

Certain medications have been developed that inhibit the nonenzymatic formation of glycation and dehydration condensation complexes in patients with the above-mentioned pathological conditions. U.S. Pat. No. 6,337,350, to Rahbar et al., discloses derivatives of aryl and heterocyclic ureido and aryl and heterocyclic carboxamido phenoxyisobutyric acids and of benzoic acid, which have been found to inhibit the nonenzymatic glycation of various proteins. Many other phenoxyisobutyric acid derivatives, as well as certain other compounds, are also disclosed that have similar beneficial effects. While it is beneficial to have these medications available for treatment, other health-related and/or disease related treatment concerns exist.

It is not uncommon for a patient suffering from multiple ailments and/or diseases to require disease specific treatment(s). If a patient is taking a specific medication treatment regime for a disease(s) (i.e., if the patient is taking at least one medication for each disease and/or more than one medication for at least one disease), this poses significant medication administration issues that must be overcome if the patient is to receive a therapeutic amount of a medication for the acquired disease(s). These issues include, but are not limited to, potential drug-drug interactions. Most often, these drug-drug interactions occur in the alimentary canal. These medication administration issues become even more complicated if the above-mentioned patient is to receive a therapeutic amount of a medication at predetermined time interval(s). Therefore, it may be necessary to deliver the medication via a parenteral route of administration or via a medical device (i.e., a medication releasably applied to a medical device, a medication releasably applied to a coating on a medical device and/or absorbed/adsorbed into or onto a coating or other surface that is either part of the medical device and/or applied to the medical device) to minimize and/or alleviate these medication administration issues. However, non-parenteral routes of administration are also acceptable, but a patient's complete medication profile must be contemplated to determine whether any potential drug-drug interactions exist.

In light of various patient specific factors, administration of these medicaments remains challenging. Moreover, administration of these medications has not been achieved in conjunction with a medical device prior to applicant's discovery. Applicant has surprisingly discovered effective methods of administration of these medications and also discovered medication releasing medical devices, wherein at least a portion of the medical device releasably includes, or is releasably coated with, medication(s) that inhibit the nonenzymatic formation of glycation and dehydration condensation complexes known as advanced glycation end-products.

SUMMARY OF THE INVENTION

The present invention relates to methods of administering medication(s) that inhibit the nonenzymatic formation of glycation and dehydration condensation complexes known as advanced glycation end-products (AGE). The present invention also relates to medication releasing medical devices, wherein at least a portion of the medical device releasably includes at least one medication(s) that inhibits the nonenzymatic formation of glycation and dehydration condensation complexes.

In one embodiment of the present invention, a method is provided for administering a medication that inhibits the nonenzymatic formation of glycation and dehydration condensation complexes known as advanced glycation end-products (AGE) to a subject in need thereof, comprising providing at least one medication that inhibits the nonenzymatic formation of AGE complexes; and administering the medication to an animal wherein the nonenzymatic formation of AGE complexes is inhibited.

In another embodiment of the method, the administering step comprises a route of administration selected from the group consisting of oral, sublingual, intravenous, intracardiac, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal and urethral. In another embodiment, the administering step comprises providing the medication on an implantable medical device.

In another embodiment, the subject is suffering from a disease selected from the group consisting of diabetes, cardiovascular disease, kidney and kidney disease, retinopathy, neuropathy or other neurological diseases including Alzheimer's disease.

In yet another embodiment, the medication is selected from the group consisting of aminoguanidine, OPB-9195 [(+/−)-2-isopropylidenehydrazono-4-oxo-thiazolidin-5-yla cetanilide], pyridoxamine, antioxidants, N-phenacylthiazolium bromide, antihypertensive drugs, angiotensin-converting enzyme inhibitors, angiotensin II receptor-1 antagonists and alagebrium. In another embodiment, the medication further comprises at least one inert pharmaceutical excipient.

In another embodiment of the present invention, a medical device is provided comprising at least one medication that inhibits the nonenzymatic formation of glycation and dehydration condensation complexes known as AGE.

In another embodiment, the medical device is selected from the group consisting of implantable medical devices, deposition implants, topical medical devices and medication delivery pumps. In another embodiment, the implantable medical device is a stent. In another embodiment, the topical medical device is selected from the group consisting of patches, gauze, wraps, appliqués, dressings and coverings.

In another embodiment, the medication is selected from the group consisting of aminoguanidine, OPB-9195 [(+/−)-2-isopropylidenehydrazono-4-oxo-thiazolidin-5-yla cetanilide], pyridoxamine, antioxidants, N-phenacylthiazolium bromide, antihypertensive drugs, angiotensin-converting enzyme inhibitors, angiotensin II receptor-1 antagonists and alagebrium.

In yet another embodiment, the medication is releasable applied to at least a portion of the surface of the device. In another embodiment, the medication is incorporated into the medical device material. In another embodiment, the medication is released from the medical device in a controlled-release manner.

These and other aspects, advantages and features of the invention will be more fully understood and appreciated by reference to the written specification and claims.

BRIEF DESCRIPTION OF THE DRAWINGS

FIG. 2 depicts the solubility of collagen treated with AGE-breakers in weak acetic acid.

DEFINITION OF TERMS

Figure 1:
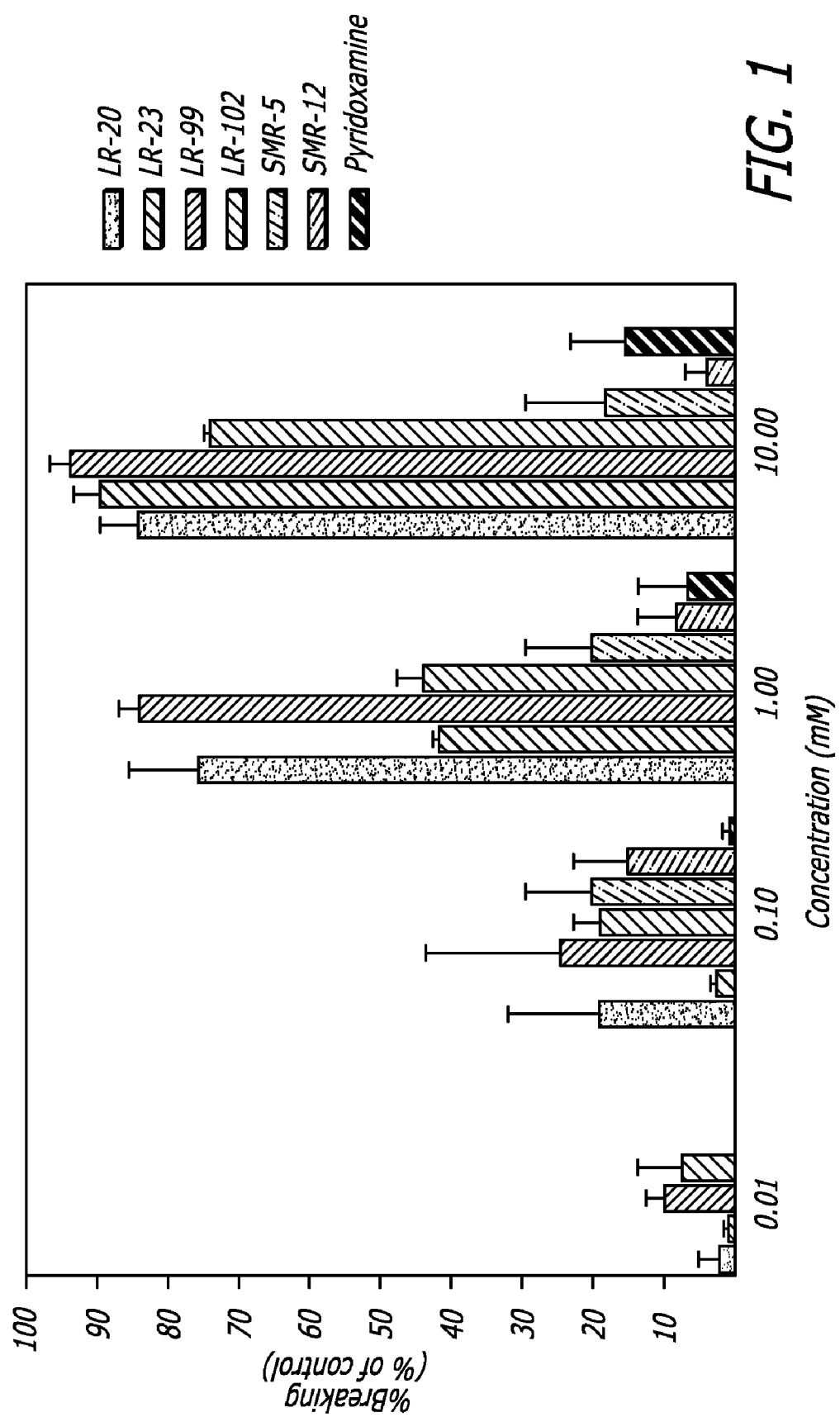
FIG. 1 depicts breaking of advanced glycosylation end products (AGEs).
Figure 3B:
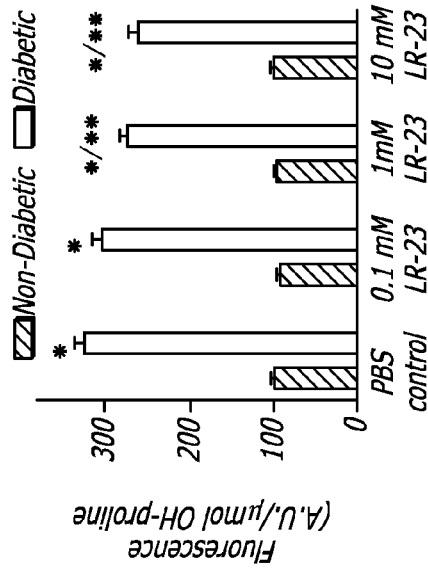
FIG. 3 depicts pepsin digestion of collagen treated with AGE-breakers.
Figure 3D:
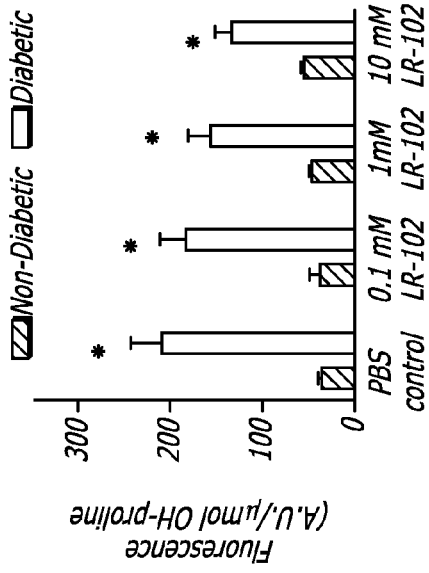
Figure 3A:
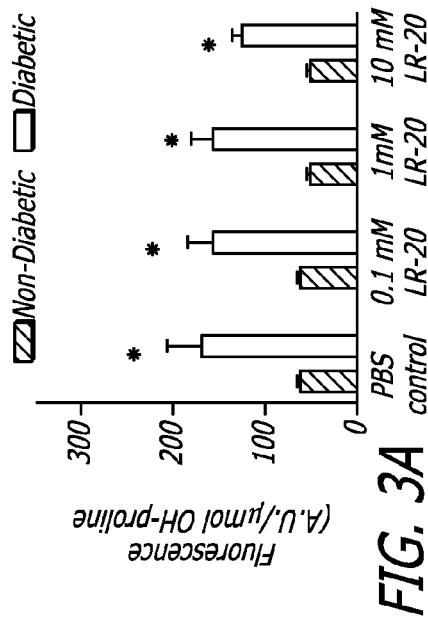
Figure 3C:
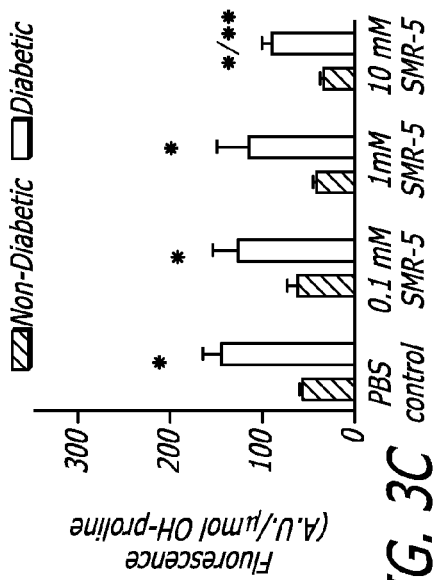
Figure 4A:
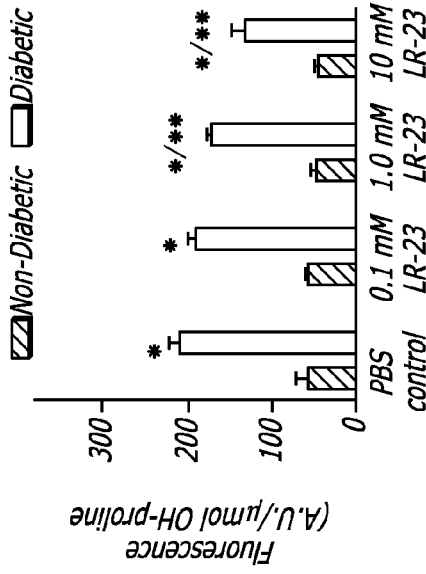
FIG. 4 depicts papain digestion of collagen treated with AGE breakers.
Figure 4B:
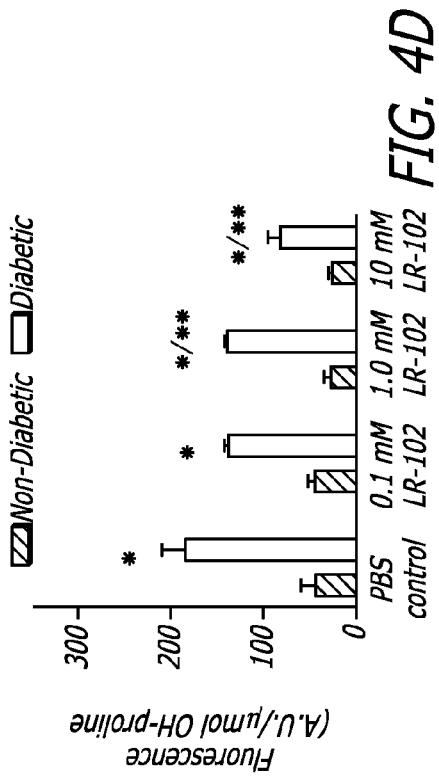
Figure 4C:
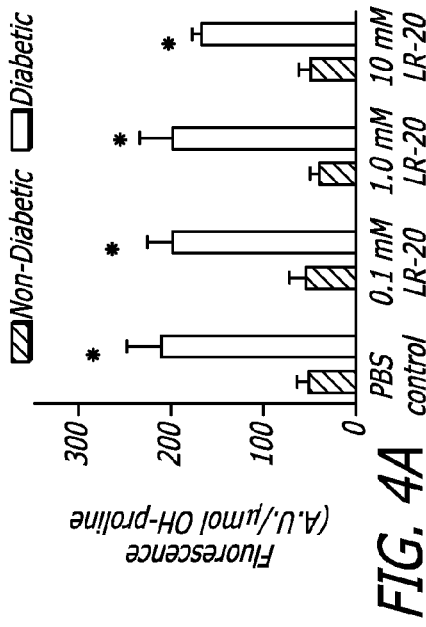
Figure 4D:
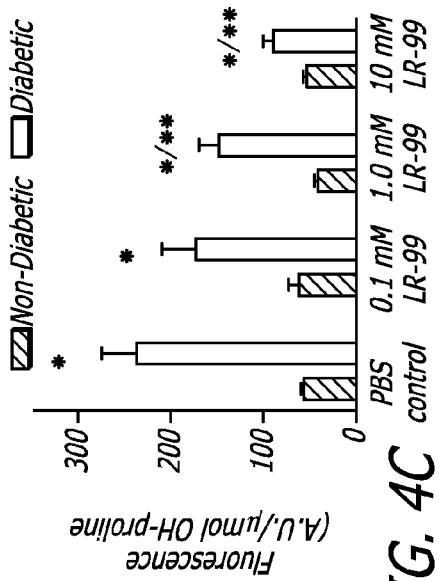

Prior to setting forth the invention, it may be helpful to define certain terms that may be used hereinafter:

Animal: As used herein "animal" shall include mammals, fish, reptiles and birds. Mammals include, but are not limited to, primates, including humans, dogs, cats, goats, sheep, rabbits, pigs, horses and cows;

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis;

Controlled release: As used herein "controlled release" refers to the release of a medication (see definition below) from a medical device at a predetermined rate. Controlled release implies that the medication does not release from the medical device sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of medication may be desirable followed by a more gradual release thereafter. The release rate may be steady state (commonly referred to as "timed release" or zero order kinetics), that is the medication is released in even amounts over a predetermined time (with or without an initial burst phase) or may be a gradient release. A gradient release implies that the concentration of medication released from the device surface changes over time;

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Delayed Release: As used herein "delayed release" refers to the release of medication(s) after a period of time and/or after an event or series of events; and Medication(s): As used herein "medication(s)" and "medication" refers to one or more drugs, pharmacologic agents or bioactive agents that inhibit the nonenzymatic formation of glycation and dehydration condensation complexes (i.e., AGEs), either alone or in combination with at least one inert pharmaceutical excipient. Also, as used herein, "medication (s)" may also refer to one or more drugs, pharmacologic agents or bioactive agents that block and/or break the formation of AGEs, either alone or in combination with at least one inert pharmaceutical excipient. Examples include proteins and peptides, polysaccharides, nucleic acids, lipids and lipopolysaccharides, and organic molecules having biological activity.

Modulate: As used herein, "modulate" refers to compounds which bind in any manner to the RAGE receptor including, but not limited to, inhibitors, agonists and antagonists.

DETAILED DESCRIPTION OF THE INVENTION

One embodiment of the present invention relates to methods of administering medication(s) that inhibit the nonenzymatic formation of advanced glycosylation end-products (AGEs) and prevent or break AGE-protein crosslinks.

Several other potential drug candidates as AGE inhibitors or breakers have been reported recently. These studies evaluated the agent's ability to inhibit AGE formation and inhibit or break AGE-protein crosslinking compared to that of aminoguanidine (AG) through in vitro and in vivo evaluations. One compound, N-phenacylthiazolium bromide (PTB), selectively cleaves AGE-derived protein crosslinks in vitro and in vivo. The pharmacological ability to break irreversible AGE-mediated protein crosslinking offers potential therapeutic use. The use of AGE inhibitors and breakers is further discussed in a review article by Rahbar and Figarola (Curr Med Chem—Imun Endoc & Metab Agents, 2:135-161, 2002) which is incorporated by reference herein for all it contains regarding AGE inhibitors and breakers.

The medications that inhibit the non-enzymatic formation of AGEs and/or prevent or break AGE-protein crosslinks can be used for the prevention or treatment of diseases and disorders, for the prevention of age-associated deterioration of heath and or tissues and cosmetic or nutriceutical applications.

Another embodiment of the present invention relates to medication releasing medical devices, wherein at least a portion of the medical device releasably includes, or is releasably coated with, a medication(s). More specifically, the present invention relates to medical devices, at least a portion of which releasably includes a medication(s) that inhibits the nonenzymatic formation of AGEs or breaks AGE-protein cross-links. These medication(s) have been shown to inhibit the non-enzymatic glycation of proteins, which otherwise would result in the formation of AGEs. The lack of AGE formation or the reduction of AGEs reduces and/or eliminates the AGE-related complications associated with some of the following diseases including, but not limited to, aging, diabetes mellitus, rheumatoid arthritis, Alzheimer's Disease, uremia and in atherosclerosis in persons undergoing hemodialysis. These same medications may be efficacious in wound healing.

Modulation of the receptor for advanced glycation end-products (RAGE) can also impact the progression of AGE-related diseases. Therefore compounds which modulate the RAGE receptor are considered within the scope of the present invention. In one embodiment of the present invention, a method is provided for modulating the advanced glycation end-product receptor (RAGE) in a subject in need thereof, comprising providing at least one medication that modulates RAGE, and administering the medication to an animal wherein said RAGE is modulated.

Furthermore, certain of the AGE inhibitors and breakers disclosed herein are peroxisome proliferator-activated receptor (PPAR) agonists (both alpha and gamma). PPARs are ligand-activated transcription factors that regulate cell growth, inflammation, lipid metabolism and insulin sensitivity. These compounds therefore have use in treating inflammatory conditions. Furthermore, PPAR agonists inhibit matrix metalloproteinases (MMPs) which are responsible for breakdown of extracellular matrix, among other activities.

Method of Administration

While any medication that inhibits the nonenzymatic formation of AGEs or modulates RAGE is contemplated herein, suitable compounds are disclosed in patents to Lalezari et al. including U.S. Pat. Nos. 5,472,981; 5,498,708; 5,962,651; 6,072,072; 4,921,997; 5,093,367; 5,268,500 and 5,292,935, which are each incorporated herein by reference in their entirety. Additionally, patents and patent applications by Rahbar et al. including U.S. Pat. Nos. 6,337,350; 6,589,944; 6,605,642; 6,787,566 and 7,030,133, U.S. Patent Publication No. 2005/0171150, and U.S. Provisional Patent Application No. 60/734,763 are each incorporated by reference herein in their entirety. More specifically, each of these above-noted U.S. patents is incorporated by reference as to the subject matter contained within each regarding the specific methods and compounds respectively disclosed.

The compounds of the present invention collectively are defined as derivatives of aryl and heterocyclic ureido and aryl and heterocyclic carboxamido phenoxy isobutyric acids (Rahbar et al., Biochem Biophys Res Commun 262:651-6, 1999). Representative compounds of the suitable for use in the present invention are identified as LR1 to LR115 (see U.S. Pat. Nos. 6,337,350, 6,605,642 and 7,030,133). For purposes of this disclosure, the names assigned to these structures are: LR1 4-[3-(6-chloro-2,4-(1H, 3H) quinazolinedione)]phenoxyisobutyric acid, MW=374.5; LR2 4-(2-furoylcarboxamido)phenoxyisobutyric acid, MW=289; LR3 4-(3,5-dichlorophenylureido) phenoxyisobutyric acid, MW=383; LR4 4-(4-ethylcarbamatophenylureido) phenoxyisobutyric acid, MW=401; LR5 4-(3,4-dichlorophenylureido)phenoxyisobutyric acid, MW=383; LR6 4-cyclohexylureidophenoxyisobutyric acid, MW=318; LR7 4-(2,3-dichlorophenylureido)phenoxyisobutyric acid, MW=383; LR8 4-(4-carboxaldehydrophenylureido)phenoxyisobutyric acid, MW=328; LR9 4-(2-naphthylcarboxamido)phenoxyisobutyric acid, MW=341; LR10 4-(4-methoxyphenylureido)phenoxyisobutyric acid, MW=344; LR11 4-(3,4-dimethoxyphenylureido)phenoxyisobutyric acid, MW=374; LR12 4-(4-chloro-3-nitrophenylureido)phenoxyisobutyric acid, MW=393.5; LR13 4-(4-methylphenylureido)phenoxyisobutyric acid, MW=328; LR14 4-(3,4,5-trimethoxyphenylureido)phenoxyisobutyric acid, MW=404; LR15 4-(3-chlorophenylureido)phenoxyisobutyric acid, MW=348.5; LR16 N-4-(nitrophthalimido)phenoxyisobutyric acid, MW=378; LR17 4-(2-thienylcarboxamido)phenoxyisobutyric acid, MW=305; LR18 4-(4-pyridylureido)phenoxyisobutyric acid, MW=300; LR19 4-(3,4,5-trichlorophenylureido)phenoxyisobutyric acid, MW=417.5; LR20 L-bis-[4-(4-chlorobenzamidophenoxyisobutyryl)cystine], MW=871; LR21 4-(3,5-dichlorophenylureido)phenoxyisobutyrylamidomethylcyclohexyl-4-carboxylic acid, MW=522; LR22 DL-N-4-[(3,5-dichlorophenylureido)phenoxyisobutyryl]pipecolic acid, MW=494; LR23 4-(3,5-dichlorophenylureido)phenoxyisobutyryl-1-amidocyclohexane-1-carboxylic acid, MW=508; LR24 4-(4-iodophenylureido)phenoxyisobutyric acid, MW=440; LR25 4-(4-dimethylaminophenylureido) phenoxyisobutyric acid, MW=345; LR26 4-(2,4,6-trichlorophenylureido)phenoxyisobutyric acid, MW=417.5; LR27 4-(2,4,6-trimethylphenylureido)phenoxyisobutyric acid, MW=356; LR28 4-(4-chlorophenoxyacetamido)phenoxyisobutyric acid, MW=363.5; LR29 4-(4-chloro-3-nitrobenzoylcarboxamido)phenoxyisobutyric acid, MW=406.5; LR30 4-chlorodiphenylurea-4'-carboxylic acid, MW=290.5; LR31 4-(3,4-dichlorophenylacetamido)phenoxyisobutyric acid, MW=382; LR32 diphenylurea-4-carboxylic acid, MW=240; LR33 4-(2-chloro-4-nitrophenylureido)phenoxyisobutyric acid, MW=393.5; LR34 4-(nicotinylamido)phenoxyisobutyric acid, MW=300; LR35 4-chlorophenoxyisobutyric acid, MW=208.5; LR36 4-(benzylsulfonamido)phenoxyisobutyric acid, MW=349; LR37 4-(2,5-dichlorobenzoylcarboxamido)phenoxyisobutyric acid, MW=396; LR38 L-4-chlorobenzoylphenylalanine, MW=303.5; LR39 2-isopropyl-5-methylphenoxyisobutyric acid, MW=236; LR40 4-(3,4-dimethoxyphenylureido)phenoxyisobutyric acid, MW=374; LR41 4-(3-chloro-4-fluorophenylureido)phenoxyisobutyric acid, MW=393.5; LR42 4-(3,5-dichlorobenzamidoethyl)phenoxyisobutyric acid, MW=384; LR43 4-(phenylureido)phenoxyisobutyric acid, MW=314; LR44 4-(phenylureido-2-chloro)phenoxyisobutyric acid, 348.5; LR45 4-(2,6-dichloro-4-nitrobenzoylcarboxamido)phenoxyisobutyric acid, MW=406.5; LR46 4-(3,5-difluorophenylureido)phenoxyisobutyric acid, MW=350; LR47 4-(N-methyl-4-chlorobenzamido)phenoxyisobutyric acid, MW=347.5; LR48 4-(4-nitrophenylureido)phenoxyisobutyric acid, MW=359; LR49 4-(phenylureido)phenoxyacetic acid, MW=286; LR50 4-(4-chlorobenzoylcarboxamido) phenoxyisobutyric acid, MW=351.5; LR51 4-(2-hydroxy-4-chlorobenzoylcarboxamido)phenoxyisobutyric acid, MW=377.5; LR52 4-(2-hydroxy-3,5-dichlorobenzoylcarboxamido)phenoxyisobutyric acid, MW=412; LR53 4-(2-chloro-5-nitrophenylureido)phenoxyisobutyric acid, MW=393.5; LR54 4-carboxyphenoxyisobutyric acid, MW=224; LR55 4-(4-carboxyphenylureido)phenoxyisobutyric acid, MW=358; LR56 4-ureidophenoxyisobutyric acid, MW=236; LR57 urea 1,3-bis-4-phenoxyisobutyric acid, MW=416; LR58 4-(4-morpholinosulfonylphenylureido) phenoxyisobutyric acid, MW=463; LR59 4-[(3,4-dichlorophenylmethyl)-2-chlorophenylureido]phenoxyisobutyric acid, MW=507.5; LR60 4-(3-pyridylureido)phenoxyisobutyric acid, MW=315; LR61 4-[(3,5-dichlorobenzoylamino)methyl]phenoxyisobutyric acid, MW=382; LR62 4-(2,4-dichlorophenacylamino)phenoxyisobutyric acid, MW=382; LR63 4-(benzylureido)phenoxyisobutyric acid, MW=328; LR64 4-acetamidobenzoic acid; LR65 2-chloro-4-acetamidobenzoic acid; LR66 4-aminophenoxyisobutyric acid; LR67 4-acetoxybenzoic acid; LR68 4-hydroxybenzoic acid; LR69 2-acetamidoterephthalic acid; LR70 5-chloro-2-acetoxybenzoic acid; LR71 2-acetamido-5-acetoxybenzoic acid; LR72 2-acetoxy-5-hydroxybenzoic acid; LR73 2-amino-5-hydroxybenzoic acid; LR74 2-(8-quinolinoxy) propionic acid; LR75 4-aminobenzoylglycine; LR76 N-guanylguanidino-N'-4-phenoxyacetic acid; LR77 2-(2,5-dichlorophenoxy)propionic acid; LR78 4-dimethylaminobenzoic acid; LR79 2-amino-4,5-dimethoxybenzoic acid; LR80 4-sulfonamidobenzoic acid; LR81 2-amino-4-chlorobenzoic acid; LR82 4-hydroxyphenylbutyric acid; LR83 2-methyl-4-quinolinecarboxylic acid; LR84 2-methyl-3,4-quinolinedicarboxylic acid; LR85 6-bromo-2-methyl-3,4-quinolinedicarboxylic acid; LR86 4-acetamidophenoxyacetic acid; LR87 1-(4-chlorophenoxybutyrylamido)-1-cyclohexanecarboxylic acid; LR88 4-chlorophenylaminocarbonyliminodiacetic acid; LR89 3-chloro-4-nitrophenylureidophenoxyisobutyric acid; LR90 methylene bis[4,4'-(2-chlorophenylureidophenoxyisobutyric acid)]; LR91 N,N'-bis (2-chloro-4-carboxyphenyl)formamidine; LR92 N,N'-bis(2-carboxyphenyl)formamidine; LR93 1-[4-chlorophenoxyisobutyrylamido]1-cyclohexane carboxylic acid; LR94 DL-4-(3,5-dichlorophenylureidophenoxyisobutyrylpiperidine)-2-carboxylic acid; LR95 L-4-(3,5-dichlorophenylureidophenoxyisobutyryl)leucine; LR96 L-4-(3,5-dichlorophenylureidophenoxyisobutyryl)glutamic acid gamma methyl ester; LR97: gamma-4-(3,5-dichlorophenylureidophenoxyisobutyrylamido) butyric acid; LR98 4-(3,5-dichlorophenylureidophenoxyisobutyrylamido) acetic acid; LR99 4-(3,5-dichlorophenylureidophenoxyisobutyryl)-4 amino benzoic acid; LR100 1,4-(3,5-dichlorophenylureidophenoxyisobutyrylamido)-1-cyclopentane carboxylic acid; LR101 1,4-benzene-bis-(ureidophenoxyisobutyric acid); LR102 1,4-benzene-bis-(4-methyleneaminophenoxyisobutyric acid); LR103 1-[(4-chlorobenzyl)-3-(3,4-dichlorophenylureido)]-4-phenoxyisobutyric acid; LR104 4-(4-fluoro-3-chlorophenylurido) phenoxyisobutyrylamidophenyl-2-carboxylic acid; LR105 1-[(2-fluoro-6-chlorobenzyl)-3-(3,4-dichlorophenylureido)]-4-phenoxyisobutyric acid; LR106 4-(4-chlorobenzylaminophenoxyisobutyric)acid; LR107 2-chlorobenzene-1,4-bis(4-ureidophenoxyisobutyric acid); LR108 1-[(4-chlorobenzyl)-3-(3,5-dichlorophenylureido)]-4-phenoxyisobutyric acid; LR109 1-[(2-fluoro-6-chlorobenzyl)-3-(2-fluoro-6-chlorophenylureido)]-4-phenoxy-isobutyric acid; LR110 4-(1,2,3,4-tetrahydroacridine-9-carboxamidophenoxyisobutyric)acid; LR111 8-quinolinoxy acetic acid; LR112 4,4'-bis[(methyleneoxyethyleneamino)phenoxy]isobutyric acid; LR113 L-8-quinolinolyl(acetylhistidine); LR114 4-[(3,5-dichlorophenylureido) phenoxyisobutyrylamido]-2-hydroxybenzene-4-carboxylic acid; and LR115 L, α-4-[(3,5-dichlorophenylureido)phenoxyisobutyrylamido] phenylalanine.

In one embodiment, the medication(s) utilized within the present invention are parameter specific medications. That is to say, generally, these medication(s) will be administered only if a patient's measured diagnostic levels are not within a given range, or if there are other diagnostic and/or determinative factors that warrant the administration of the medication. For example, one diagnostic and/or monitoring test that may be administered to a patient is the glycolated hemoglobin test (HbA1c, also called hemoglobin A1c or the glycosylated hemoglobin test). This test is a blood test to determine control of a patient's diabetes. It provides an average blood glucose measurement (typically, over the previous six to twelve weeks) and typically is used in conjunction with home glucose monitoring to make treatment adjustments. The normal range for the HbA1c test is between about 4 percent and about 6 percent for people without diabetes. The preferred range for people with diabetes is generally less than about 7 percent, and an acceptable range for people with diabetes is less than about 8 percent. Typically, patients with diabetes who are treated with insulin should have this glycolated hemoglobin test administered about four times a year (every 3 months). The test may be needed more frequently if the diabetes is not well controlled. Those who are not treated with insulin should have this test about every four to six months.

Another common diagnostic and/or monitoring test that may be administered to patients is an albumin test. This test measures the amount of protein in a patient's urine. If abnormally high levels of protein are present in the urine, this is typically an indication of kidney damage or it may be indicative of other internal damage and/or disease states. Also, if abnormally high levels of proteins are present in the urine, an appropriate treatment regime may be initiated to treat the kidney damage and/or the underlying cause of the kidney damage.

The aforementioned two tests, among others, may be used to select the appropriate dosage, dosage time interval and/or route(s) of administration for a given patient.

While these medications are typically parameter specific medications, they may be efficacious in wound healing. For example, a compound that inhibits the formation of AGE complexes may be applied to, or incorporated within, a medical device (i.e., a wound dressing, patch, etc.) and applied to a patient's skin to aid the wound healing process.

In another, non-limited example, a compound that modulates RAGE is applied to a wound in a medical device.

However, the medications of the present invention can be used for other medicinal or cosmetic indications and are not parameter specific. Therefore they can be administered or used at the discretion of a medical professional or a subject.

Any method of administering the medication(s) discussed herein is contemplated. While it is understood by one skilled in the art that the method of administration may depend on patient specific factors, the methods of administration include, but are not limited to, generally parenteral and non-parenteral administration. More specifically, the routes of administration include, but are not limited to oral, sublingual, intravenous, intracardiac, topical, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal, urethral, etc. When the route of administration is topical, the medications and compositions disclosed herein can be administered to any surface or part of the body.

Of course, it is understood that the medication will be administered in the appropriate dosage, depending on the route of administration. For example, an oral dosage form may be administered in at least one of the following dosage forms: tablet; capsule; solution; syrup; elixir; suspension; magma; gel; food product and/or powder. A sublingual preparation may be administered in at least one of the following dosage forms: tablet; troche; and/or lozenge. A parenteral dosage form may be administered in at least one of the following dosage forms: solution and/or suspension. An epicutaneous/transdermal dosage form may be administered in at least one of the following dosage forms: ointment; cream; infusion pump; paste; plaster; powder; aerosol; lotion; transdermal patch/disc/solution. A conjunctival dosage form may be administered in at least one of the following dosage forms: contact lens insert and/or ointment. An intraocular/intramural dosage form may be administered in at least one of the following dosage forms: solution and/or suspension. An intranasal dosage form may be administered in at least one of the following dosage forms: solution; spray; inhalant and/or ointment. An intrarespiratory dosage form may be administered in at least one of the following dosage forms: aerosol and/or powder. A rectal dosage form may be administered in at least one of the following dosage forms: solution; ointment and/or suppository. A vaginal dosage form may be administered in at least one of the following dosage forms: solution; ointment; emulsion foam; tablet; insert/suppository/sponge. A urethral dosage form may be administered in at least one of the following dosage forms: solution and/or suppository.

For example, the medications can be formed into syrups or other solutions for administration orally, for example health drinks, in the presence of one or more excipients selected from sugars, vitamins, flavoring agents, coloring agents, preservatives and thickeners. Additionally, the medications can be formulated in a food product such as, but not limited to, a snack bar. For presentation in the form of snack food bars, the medications can be admixed with any one or more ingredients selected from dried fruits, nuts and cereals The medications can also be provided in a powder form for reconstitution as a solution. As such they can also contain soluble excipients such as sugars, buffering agents such as citrate and phosphate buffers, and effervescent agents formed from carbonates, e.g bicarbonates such as sodium or ammonium bicarbonate, and a solid acid, for example citric acid or an acid citrate salt.

The medications can be presented as food supplements or food additives, or can be incorporated into foods, for example functional foods or nutriceuticals.

The above-noted dosage form(s) may include at least one medication disclosed herein, either alone or in combination with at least one other medication disclosed herein or with a medication not disclosed herein and/or in combination with at least one inert pharmaceutical excipient. These medications may have any release profile including, but not limited to, an immediate release, a controlled release and/or a delayed release profile. A controlled release profile is typically preferred.

While any medication as defined above may be used in the present invention, examples of medications that inhibit the formation of AGEs and/or modulate RAGE include, but are not limited to aminoguanidine, OPB-9195 [(+/−)-2-isopropylidenehydrazono-4-oxo-thiazolidin-5-yla cetanilide], pyridoxamine, antioxidants, N-phenacylthiazolium bromide, antihypertensive drugs, angiotensin-converting enzyme inhibitors and angiotensin II receptor-1 antagonists, alagebrium, pentoxifylline, pioglitazone, metformin, compounds LR1 through LR115, etc.

AGEs, and AGE-modified proteins increase with aging and contribute to normal tissue remodeling and aging. Therefore, the AGE inhibitors or breakers may be used for the treatment of normal age-relating changes to tissues. One potential use is in cosmetic applications to treat age-induced changes in the skin. The AGE inhibitors and breakers disclosed herein break AGE-collagen crosslinks, measured by increases in collagen solubility. Therefore these AGE inhibitors and breakers may reverse some age-related changes in skin.

In one embodiment of the present invention, the AGE inhibitors and breakers are formulated as a sunscreen.

In another embodiment of the present invention, the AGE inhibitors and breakers are formulated as an eye cream.

In yet another embodiment, the AGE inhibitors or breakers of the present invention may be formulated for cosmetic use as a topical preparation. The cosmetic compositions of the present invention may be formulated in a wide variety of forms including, but not limited to, a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In another embodiment of the present invention, the AGE inhibitors and breakers are formulated as a cosmeceutical. Furthermore, the AGE inhibitors and breakers are formulated for administration to the hair or to the scalp. In another embodiment, the AGE inhibitors and breakers are formulated The cosmetically acceptable carrier contained in the present cosmetic composition, may be varied depending on the type of the formulation. For example, the formulation of ointment, pastes, creams or gels may comprise carriers including, but not limited to, animal and vegetable fats, waxes, paraffins, starch, tragacanth, cellulose derivatives, polyethylene glycols, silicones, bentonites, silica, talc, zinc oxide or mixtures of these substances. In the formulation of powder or spray, it may comprise compounds including, but not limited to, lactose, talc, silica, aluminum hydroxide, calcium silicate, polyamide powder and mixtures of these substances. Spray may additionally comprise the customary propellants including, but not limited to, chlorofluorohydrocarbons, propane/butane or dimethyl ether.

The formulation of solution and emulsion may comprise solvent, solubilizer and emulsifier including, but not limited to, water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents including, but not limited to, water, ethanol or propylene glycol, suspending agents, for example ethoxylated isostearyl alcohols, polyoxyethylene sorbitol esters and poly oxyethylene sorbitan esters, microcrystalline cellulose, aluminum metahydroxide, bentonite, agar and tragacanth or mixtures of these substances.

The formulation of soap may comprise components including, but not limited to, alkali metal salts of fatty acids, salts of fatty acid hemiesters, fatty acid protein hydrolyzates, isethionates, lanolin, fatty alcohol, vegetable oil, glycerol, sugars or mixtures of these substances.

Furthermore, the cosmetic compositions may contain excipients as well as carrier. The non-limiting examples of excipients include preservatives, antioxidants, stabilizers, solubilizers, vitamins, colorants, odor improvers or mixtures of these substances In the pharmaceutical compositions of the AGE inhibitors and breakers, the pharmaceutically acceptable carrier may be conventional one for formulation, including, but not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxy benzoate, propylhydroxy benzoate, talc, stearic acid, magnesium and mineral oil, but not limited to. The pharmaceutical compositions may further contain other agents, including but not limited to, wetting agent, sweetening agent, emulsifying agent, suspending agent, preservatives, flavors, perfumes, lubricating agent, or mixtures of these substances.

Medication Releasing Medical Device

The medical devices considered herein may be any known medical device. Some examples include, but are not limited to, implantable medical devices such as, but not limited to, stents (both vascular and urethral), deposition implants (implantable medication releasing device), and/or a medication delivery pumps. Also, contemplated herein are topically applied medical devices including, but not limited to, patches, gauze, wraps, appliqués, dressings, coverings, etc. In the case of a medical device, at least one medication may be releasably applied either to at least a portion of the surface of the device, or to a material applied to the surface of a device. Alternatively, at least one medication may be absorbed and/or adsorbed into or onto the device material so long as the medication may be released from the material at a later time.

The medication may be releasably applied to the medical device via any industrially acceptable method, including, but not limited to, spray coating, a waterfall method, heat annealing, etc., however, spray coating is typically preferred. Alternatively, the medical device may include at least one medication, wherein the medication is absorbed and/or adsorbed into or onto the medical device. This may be done by any industrially acceptable method. Also, it is contemplated herein that a medical device may include both at least one medication releasably applied to the medical device itself and/or a coating applied to the device and at least one medication absorbed and/or adsorbed into or onto the medical device itself.

EXAMPLE 1

Effects of Age-Breakers on Collagen

FIG. 1 demonstrates the concentration dependent AGE-breaking properties of six compounds and pyridoxamine. Certain of these compounds demonstrated AGE-breaking effects at 10 and 100 micromolar concentrations. Specifically, bovine serum albumin (10 mg/mL) was incubated with 0.5 M ribose in 0.4 M phosphate buffer, pH 7.5, containing 0.02% sodium azide for 24 hr at 37° C., followed by extensive dialysis for 24 hr at 4° C. to remove excess and reversibly bound ribose. AGE formation was then initiated by incubating 0.1 mg/mL (or 1:100 dilution in phosphate buffer) of the glycated protein at 37° C. Then the AGE formed were treated with various concentrations for the compounds for 48 hr at 37° C. Aliquots from each sample were taken and diluted with 0.1 M sodium carbonate buffer to 50 μg/mL. Then 50 μl of the diluted sample was added to wells of a 96-well polystyrene plate (1.0 μg/well) and incubated overnight at room temperature. The plates were washed thrice with PBS-0.05% Tween and blocked for 1 hr with Superblock blocking buffer. The amount of AGE in each treatment was then quantified by ELISA using polyclonal anti-AGE-RNAse antibodies. Percent AGE-breaking was calculated as: (100*(mean OD wells of control-mean OD wells with compound/mean OD wells control).

The effects of these compounds on AGE crosslinks that form in vivo in tail tendon collagen of old diabetic rats were determined. Non-diabetic rats served as controls. P values were calculated using unpaired Student's t-test. The extent of AGE crosslinking of tail tendon collagen formed in vivo was assessed by acid insolubility (FIG. 2, * $P<0.05$ vs. non-diabetic control; ** $P<0.05$ vs. diabetic control) and fluorescence measurements of collagen treated with AGE-breakers after pepsin (FIG. 3; * $P<0.05$ vs. diabetic control) or papain digestion (FIG. 4; * $P<0.05$ vs. non-diabetic control; ** $P<0.05$ vs. diabetic control). In each of FIGS. 2-4, panel A is LR-20, panel B is LR-23, panel C is LR-99 and panel D is LR-102. In all three figures, treatment of collagen with the compounds, particularly at 1.0 and 10 mM concentrations, resulted in increased collagen solubility and reduction of fluorescence associated with AGE crosslinks.

Unless otherwise indicated, all numbers expressing quantities of ingredients, properties, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents in this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method for the inhibition of the nonenzymatic formation of glycation and dehydration condensation complexes in a subject of said inhibition said method comprising administering to said subject at least one medication that inhibits the nonenzymatic formation of AGE complexes wherein said medication is administered topically and said medication is selected from the group consisting of pyridoxamine, N-phenacylthiazonium bromide, algaebrium, 4-[3-(6-chloro-2,4-(1H,3H)quinazolinedione)]phenoxyisobutyric acid, 4-(2-furoylcarboxamido)phenoxyisobutyric acid; 4-(3,5-dichlorophenylureido)phenoxyisobutyric acid; 4-(4-ethyl-carbamatophenylureido)phenoxyisobutyric acid; 4-(3,4-dichlorophenylureido)phenoxyisobutyric acid; 4-cyclohexylureidophenoxyisobutyric acid; 4-(2,3-dichlorophenylureido)phenoxyisobutyric acid, 4-(4-carboxaldehydrophenylureido)phenoxyisobutyric acid, 4-(2-naphthylcarboxamido)phenoxyisobutyric acid, 4-(4-methoxyphenylureido)phenoxyisobutyric acid, 4-(3,4-dimethoxyphenylureido)phenoxyisobutyric acid, 4-(4-chloro-3-nitrophenylureido)phenoxyisobutyric acid, 4-(4-methylphenylureido)phenoxyisobutyric acid, 4-(3,4,5-trimethoxyphenylureido)phenoxyisobutyric acid; 4-(3-chlorophenylureido)phenoxyisobutyric acid, N-4-(nitrophthalimido)phenoxyisobutyric acid, 4-(2-thienylcarboxamido)phenoxyisobutyric 4-(4-pyridylureido)phenoxyisobutyric acid, 4-(3,4,5-trichlorophenylureido)phenoxyisobutyric acid, L-bis-[4-(4-chlorobenzamidophenoxyisobutyryl)cystine], 4-(3,5-dichlorophenylureido)phenoxyisobutyrylamidomethylcyclohexyl-4-carboxylic acid, DL-N-4-[(3,5-dichlorophenylureido)phenoxyisobutyryl]pipecolic acid, 4-(3,5-dichlorophenylureido)phenoxyisobutyryl-1-amidocyclohexane-1-carboxylic acid, 4-(4-iodophenylureido)phenoxyisobutyric acid, 4-(4-dimethylaminophenylureido)phenoxyisobutyric acid; 4-(2,4,6-trichlorophenylureido)phenoxyisobutyric acid; 4-(2,4,6-trimethylphenylureido)phenoxyisobutyric acid, 4-(4-chlorophenoxyacetamido)phenoxyisobutyric acid, 4-(4-chloro-3-nitrobenzoylcarboxamido)phenoxyisobutyric acid, 4-chlorodiphenylurea-4'-carboxylic acid, 4-(3,4-dichlorophenylacetamido)phenoxyisobutyric acid, diphenylurea-4-carboxylic acid, 4-(2-chloro-4-nitrophenylureido)phenoxyisobutyric acid, 4-(nicotinylamido)phenoxyisobutyric acid, 4-chlorophenoxyisobutyric acid, 4-(benzylsulfonamido)phenoxyisobutyric acid, 4-(2,5-dichlorobenzoylcarboxamido)phenoxyisobutyric acid, L-4-chlorobenzoylphenylalanine, 2-isopropyl-5-methylphenoxyisobutyric acid, 4-(3,4-dimethoxyphenylureido)phenoxyisobutyric acid, 1 4-(3-chloro-4-fluorophenylureido)phenoxyisobutyric acid, 4-(3,5-dichlorobenzamidoethyl)phenoxyisobutyric acid, 3 4-(phenylureido)phenoxyisobutyric acid, 4-(phenylureido-2-chloro)phenoxyisobutyric acid, 4-(2,6-dichloro-4-nitrobenzoylcarboxamido)phenoxyisobutyric acid, 4-(3,5-difluorophenylureido)phenoxyisobutyric acid, 4-(N-methyl-4-chlorobenzamido)phenoxyisobutyric acid, 4-(4-nitrophenylureido)phenoxyisobutyric acid, 4-(phenylureido)phenoxyacetic acid, 4-(4-chlorobenzoylcarboxamido)phenoxyisobutyric acid, 4-(2-hydroxy-4-chlorobenzoylcarboxamido)phenoxyisobutyric acid, 4-(2-hydroxy-3,5-dichlorobenzoylcarboxamido)phenoxyisobutyric acid, 4-(2-chloro-5-nitrophenylureido)phenoxyisobutyric acid, 4-carboxyphenoxyisobutyric acid, 4-(4-carboxyphenylureido)phenoxyisobutyric acid, 4-ureidophenoxyisobutyric acid, urea 1,3-bis-4-phenoxyisobutyric acid, 4-(4-morpholinosulfonyl phenylureido)phenoxyisobutyric acid, 4-[(3,4-dichlorophenylmethyl)-2-chlorophenylureido]phenoxyisobutyric acid, 4-(3-pyridylureido)phenoxyisobutyric acid, 4-[(3,5-dichlorobenzoylamino)methyl]phenoxyisobutyric acid, 4-(2,4-dichlorophenacylamino)phenoxyisobutyric acid, 3 4-(benzylureido)phenoxyisobutyric acid, 4-acetamidobenzoic acid, 2-chloro-4-acetamidobenzoic acid, 4-aminophenoxyisobutyric acid, 4-acetoxybenzoic acid, 4-hydroxybenzoic acid, 2-acetamidoterephthalic acid, 5-chloro-2-acetoxybenzoic acid, 2-acetamido-5-acetoxybenzoic acid, 2-acetoxy-5-hydroxybenzoic acid, 2-amino-5-hydroxybenzoic acid, 2-(8-quinolinoxy)propionic acid, 4-aminobenzoylglycine, N-guanylguanidino-N'-4-phenoxyacetic acid, 2-(2,5-dichlorophenoxy)propionic acid, 4-dimethylaminobenzoic acid, 2-amino-4,5-dimethoxybenzoic acid, 4-sulfonamidobenzoic acid, 2-amino-4-chlorobenzoic acid, 4-hydroxyphenylbutyric acid, 2-methyl-4-quinolinecarboxylic acid, 2-methyl-3,4-quinolinedicarboxylic acid, 6-bromo-2-methyl-3,4-quinolinedicarboxylic acid, 4-acetamidophenoxyacetic acid, 1-(4-chlorophenoxybutyrylamido)-1-cyclohexanecarboxylic acid, 4-chlorophenylaminocarbonyliminodiacetic acid, 3-chloro-4-nitrophenylureidophenoxyisobutyric acid, methylene bis[4,4'-(2-chlorophenylureidophenoxyisobutyric acid)], N,N'-bis(2-chloro-4-carboxyphenyl)formamidine, N,N'-bis(2-carboxyphenyl)formamidine, 1-[4-chlorophenoxyisobutyrylamido]1-cyclohexane carboxylic acid, DL-4-(3,5-dichlorophenylureidophenoxyisobutyrylpiperidine)-2-carboxylic acid, L-4-(3,5-dichlorophenylureidophenoxyisobutyryl)leucine, L-4-(3,5-dichlorophenylureidophenoxyisobutyryl)glutamic acid gamma methyl ester, gamma-4-(3,5-dichlorophenylureidophenoxyisobutyrylamido) butyric acid, 4-(3,5-dichlorophenylureidophenoxyisobutyrylamido) acetic acid, 4-(3,5-dichlorophenylureidophenoxyisobutyryl)-4 amino benzoic acid, 1,4-(3,5-dichlorophenylureidophenoxyisobutyrylamido)-1-cyclopentane carboxylic acid, 1,4-benzene-bis-(ureidophenoxyisobutyric acid), 1,4-benzene-bis-(4-methyleneaminophenoxyisobutyric acid), 1-[(4-chlorobenzyl)-3-(3,4-dichlorophenylureido)]-4-phenoxyisobutyric acid, 4-(4-fluoro-3-chlorophenylurido) phenoxyisobutyrylamidophenyl-2-carboxylic acid, 1-[(2-fluoro-6-chlorobenzyl)-3-(3,4-dichlorophenylureido)]-4-phenoxyisobutyric acid, 4-(4-chlorobenzylaminophenoxyisobutyric)acid, 2-chlorobenzene-1,4-bis(4-ureidophenoxyisobutyric acid), 1-[(4-chlorobenzyl)-3-(3,5-dichlorophenylureido)]-4-phenoxyisobutyric acid, 1-[(2-fluoro-6-chlorobenzyl)-3-(2-fluoro-6-chlorophenylureido)]-4-phenoxy-isobutyric acid, 4-(1,2,3,4-tetrahydroacridine-9-carboxamidophenoxyisobutyric)acid, 8-quinolinoxy acetic acid, 4,4'-bis[(methyleneoxyethyleneamino)phenoxy]isobutyric acid, L-8-quinolinolyl(acetylhistidine), 4-[(3,5-dichlorophenylureido)phenoxyisobutyrylamido]-2-hydroxybenzene-4-carboxylic acid, L-.alpha.-4-[(3,5-dichlorophenylureido)phenoxyisobutyrylamido]phenylalanine and combinations thereof.

2. The method according to claim 1 wherein said medication is administered to said subject for a cosmetic purpose.

3. The method according to claim 1 wherein said medication further comprises at least one inert pharmaceutical excipient.

4. The method according to claim 1 wherein said medication comprises a controlled-release profile.

* * * * *